(12) United States Patent
Murphy (10) Patent No.: US 7,789,246 B1
(45) Date of Patent: Sep. 7, 2010

(54) BIOLOGICAL SAMPLE COLLECTOR

(75) Inventor: Gloria A. Murphy, French Camp, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 877 days.

(21) Appl. No.: 11/706,062

(22) Filed: Feb. 13, 2007

Related U.S. Application Data

(60) Provisional application No. 60/773,732, filed on Feb. 14, 2006.

(51) Int. Cl.
*B01D 21/24* (2006.01)

(52) U.S. Cl. ...................... 210/405; 210/406

(58) Field of Classification Search .......... 210/405–406
See application file for complete search history.

(56) References Cited

U.S. PATENT DOCUMENTS

| | | | |
|---|---|---|---|
| 4,777,021 A * | 10/1988 | Wertz et al. .................. | 422/101 |
| 7,121,157 B2 | 10/2006 | Lean et al. | |
| 7,140,265 B2 | 11/2006 | McGill et al. | |
| 2004/0054286 A1 * | 3/2004 | Audain et al. ................ | 600/449 |
| 2007/0231217 A1 * | 10/2007 | Clinton et al. ............... | 422/119 |

* cited by examiner

*Primary Examiner*—Chester T Barry
(74) *Attorney, Agent, or Firm*—Fred A. Lewis; James C. Durkis (57) ABSTRACT

A biological sample collector is adapted to a collect several biological samples in a plurality of filter wells. A biological sample collector may comprise a manifold plate for mounting a filter plate thereon, the filter plate having a plurality of filter wells therein; a hollow slider for engaging and positioning a tube that slides therethrough; and a slide case within which the hollow slider travels to allow the tube to be aligned with a selected filter well of the plurality of filter wells, wherein when the tube is aligned with the selected filter well, the tube is pushed through the hollow slider and into the selected filter well to sealingly engage the selected filter well and to allow the tube to deposit a biological sample onto a filter in the bottom of the selected filter well. The biological sample collector may be portable.

25 Claims, 7 Drawing Sheets

BIOLOGICAL SAMPLE COLLECTOR

CROSS-REFERENCE TO RELATED APPLICATIONS

This application claims the priority of U.S. Provisional Application No. 60/773,732, filed on Feb. 14, 2006, the entire disclosure and contents of which is hereby incorporated by reference.

GOVERNMENT INTEREST STATEMENT

The United States Government has rights in this invention pursuant to Contract No. W-7405-ENG-48 between the United States Department of Energy and the University of California for the operation of the Lawrence Livermore National Laboratory.

BACKGROUND

1. Field of the Invention

The present invention relates generally to biological sample collectors, and more particularly to biological sample collectors used in verifying a biological decontamination protocol.

2. Related Art

After an attack involving a biological agent against a facility, authorities must act to decontaminate if the facility will be used by the public again. A variety of biological decontamination protocols may be used to clean a contaminated facility. Even though these protocols exist, the assessment of the effectiveness of a selected protocol may be time-consuming and difficult due in part to the range of weaponizable biological agents. Moreover, the correct tools and methods for identifying the presence of many biological agents are unknown, which also may slow the verification of the decontamination protocol. Furthermore, biological agents may not have a uniform susceptibility to a particular decontamination protocol.

One important aspect in verifying the efficiency of the decontamination protocol is the collection of biological samples from the environment. Samples must be collected from different surfaces within the environment and tested. Conventional devices and tools for collecting are insufficient and not suitable for all types of surfaces. For example, wipes are not suitable for collecting samples from carpet or fabric and are easily tearable. Further, the biological samples collected using these conventional devices and tools are not suited to be directly tested using a high-throughput automated process.

SUMMARY

According to a first broad aspect of the present invention, there is provided a biological sample collector comprising a manifold plate for mounting a filter plate thereon, the filter plate having a plurality of filter wells therein; a hollow slider for engaging and positioning a tube that slides therethrough; and a slide case within which the hollow slider travels to allow the tube to be aligned with a selected filter well of the plurality of filter wells, wherein when the tube is aligned with the selected filter well, the tube is pushed through the hollow slider and into the selected filter well to sealingly engage the selected filter well and to allow the tube to deposit a biological sample onto a filter in the bottom of the selected filter well.

According to a second broad aspect of the invention, there is provided a biological sample collector comprising a suction means in fluid communication with a filter plate, wherein the filter plate comprises a plurality of filter wells; a hollow slider for engaging and positioning a tube that slides therethrough; and a slide case within which the hollow slider travels to allow the tube to be aligned with a selected filter well of the plurality of filter wells, wherein when the tube is aligned with the selected filter well, the tube is pushed through the hollow slider and into the selected filter well to sealingly engage the selected filter well and to allow the suction means to pull a biological sample from the tube that is deposited on a filter in the bottom of the selected filter well.

According to a third broad aspect of the invention, there is provided a biological sample collector comprising a suction means within a housing; a manifold plate mounted on the housing for mounting a filter plate thereon, the filter plate having a plurality of filter wells therein; and a tube case having a plurality of tube holders each for engaging and positioning a tube that slides through the selected tube holder, wherein when the tube is aligned with a selected filter well of the plurality of filter wells, the tube is pushed through the selected tube holder and into the selected filter well to sealingly engage the selected filter well and to allow the suction means to pull from the tube a biological sample that is deposited on a filter in the bottom of the selected filter well.

According to a fourth broad aspect of the invention, there is provided a method for collecting one or more biological samples comprising the following steps: (a) inserting a tube into a first filter well; (b) transferring through the tube a first set of biological samples onto a first filter in said first filter well; (c) moving the tube into alignment with a second filter well; and (d) transferring through the tube a second set of biological samples onto a second filter in said second filter well.

BRIEF DESCRIPTION OF THE DRAWINGS

The invention will be described in conjunction with the accompanying drawings, in which.

DETAILED DESCRIPTION

It is advantageous to define several terms before describing the invention. It should be appreciated that the following definitions are used throughout this application. Where the definition of terms departs from the commonly used meaning of the term, applicant intends to utilize the definitions provided below, unless specifically indicated.

DEFINITIONS

For the purposes of the present invention, the term "biological agent" refers to a biological organism that is present in an environment that is not normally present, or whose presence is at levels that are higher than normal, and whose reduction, elimination, destruction or neutralization is desirable. Biological agents include existing and yet to be developed biological weapons. The range of biological organisms includes spores, bacteria, prokaryotes, viruses, yeasts, fungi, and other single cell organisms. One example of a biological agent is an anthrax, *bacillus anthracis*, spore. Note that when this application refers to collecting biological agents, this application is referring to collecting multiple biological organisms of one type of biological agent, unless otherwise indicated.

For the purposes of the present invention, the term "biological sample" refers to the material, organisms and debris collected from an environment. The biological sample may have one or more biological agents present.

For the purposes of the present invention, the term "decontamination protocol" refers to any method of cleaning, destroying, removing or killing a biological contamination from an environment. The decontamination protocol may involve a vapor, solution or physical decontamination, or combinations thereof. Examples of biological decontamination protocols include fumigation with chlorine dioxide, steam sterilization, or gamma radiation. Some current methods of decontamination involve using combinations of solutions or fumigants of sodium hypochlorite (bleach), ethylene oxide, methyl bromide, ozone, paraformaldehyde, and other antiseptics and disinfectants, as well as vacuum cleaning with HEPA filtration. Further description of decontamination protocols are provided in Berns, et al., "Reopening Public Facilities After a Biological Attack: A Decision-Making Framework," National Academies Press (2005), the entire contents and disclosures of which is hereby incorporated by reference.

For the purposes of the present invention, the term "environment" refers to a facility, building, or transport device where the presence of a biological agent has been detected. A treated environment refers to a facility or building that is in the process of being or has been cleaned using biological decontamination protocols. It should be readily understood that environment may encompass a plurality of separate buildings in an area. A transport device includes trains, buses, trolleys, subways, airplanes, ferries, cruise ships, barges, cargo ships or similar vehicles used in transportation of people and goods.

For the purposes of the present invention, the term "fluid communication" or "fluidly connected" refers to an interaction between two or more components in which a fluid is used. The fluid may comprise a liquid, gas or mixture thereof. For example the air pump is fluidly connected, using air, to the tube through the network of pipes in the manifold plate and filter well.

For the purposes of the present invention, the term "polymerase chain reaction" (PCR) refers to a method of amplifying a specific target polynucleotide through repeated cycles of DNA strand separation (denaturating), annealing of oligonucleotide primers, and DNA polymerization using a thermostable DNA polymerase. As used herein, "quantitative polymerase chain reaction" (qPCR) refers to a PCR reaction performed such that the assay is capable of quantifying the amount of target polynucleotide present in the sample. Also, as used herein "rapid viability-PCR" (RV-PCR) refers to a qPCR that determines whether a sample is viable within approximately 24 hours or less.

For the purposes of the present invention, the term "sealingly" refers to the interaction when two components are connected or engaged as being substantially air tight. Although components may be sealingly engaged when assembled, the components may be separated and reattached.

For the purposes of the present invention, the term "viable" refers to the ability of a biological organism, including biological agents, to carry out those biochemical and genetic processes that allow the organism to propagate under suitable conditions, including gene expression, i.e. transcription, and DNA and RNA replication. Organisms that require the presence of a host cell in order to propagate are considered to be "viable" so long as they are capable of propagation in the presence of a suitable host cell. Moreover, for organisms, such as viruses, and certain mycoplasmata, viability necessarily connotes infectivity, i.e., without the ability to infect a compatible host cell, such agents would be considered non-viable.

DESCRIPTION

To rapidly restore a facility following a biological agent release, i.e. in a terrorist attack, the verification method of the decontamination protocol must provide quick turn around time and reliable results to determine building safety. Aspects of the present invention provide devices and methods to collect biological samples for verifying the biological decontamination protocols using highly specific, quantitative, real-time, polymerase chain reaction (PCR) assays. The effectiveness of a protocol may be determined by whether any collected biological agents are viable after treatment using the protocol. The viability of the biological agents collected from an environment corresponds to the viability of the possible biological agents remaining in the environment. Once an effective biological decontamination protocol is verified, the authorities may confirm that a facility is clean enough to be safe.

To collect the biological agents, embodiments of the present invention provide a biological sample collector, also referred to as an Enviro CAF™. The biological sample collector may be used in both indoor and outdoor environments. One important aspect of the biological sample collector is that the collection is optimized such that the biological samples are collected directly in a filter well. This allows culturing and further testing to occur within the filter well without the need to transfer the biological sample. One advantage of such embodiments is that testing occurs within the device used to collect the biological sample. An example of testing method is described in co-pending applications entitled, "Rapid Viability Assessment of Biological Indicators by qPCR," filed on Feb. 13, 2007, Ser. No. 11/706,064, now abandoned and "Rapid Viability Assessment of Environment Samples by qPCR," filed on Feb. 13, 2007, Ser. No. 11/706,063, the entire contents and disclosures of which are hereby incorporated by reference. Such embodiments increase safety and reduce unnecessary contamination or aerosolization when collecting a biological agent.

Figure 1:
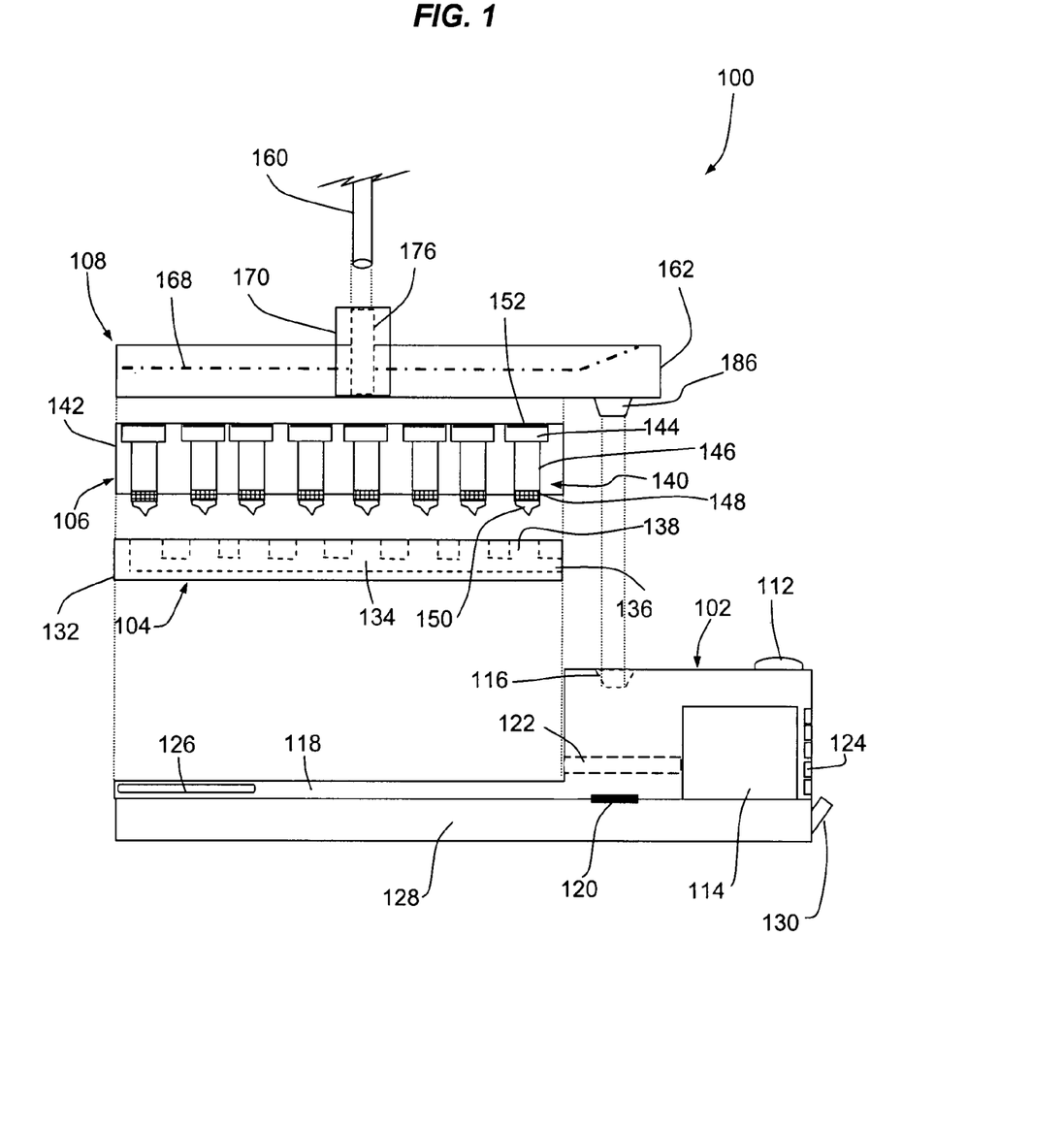
FIG. 1 is an exploded side view of a biological sample collector in accordance with an embodiment of the present invention.
Figure 2:
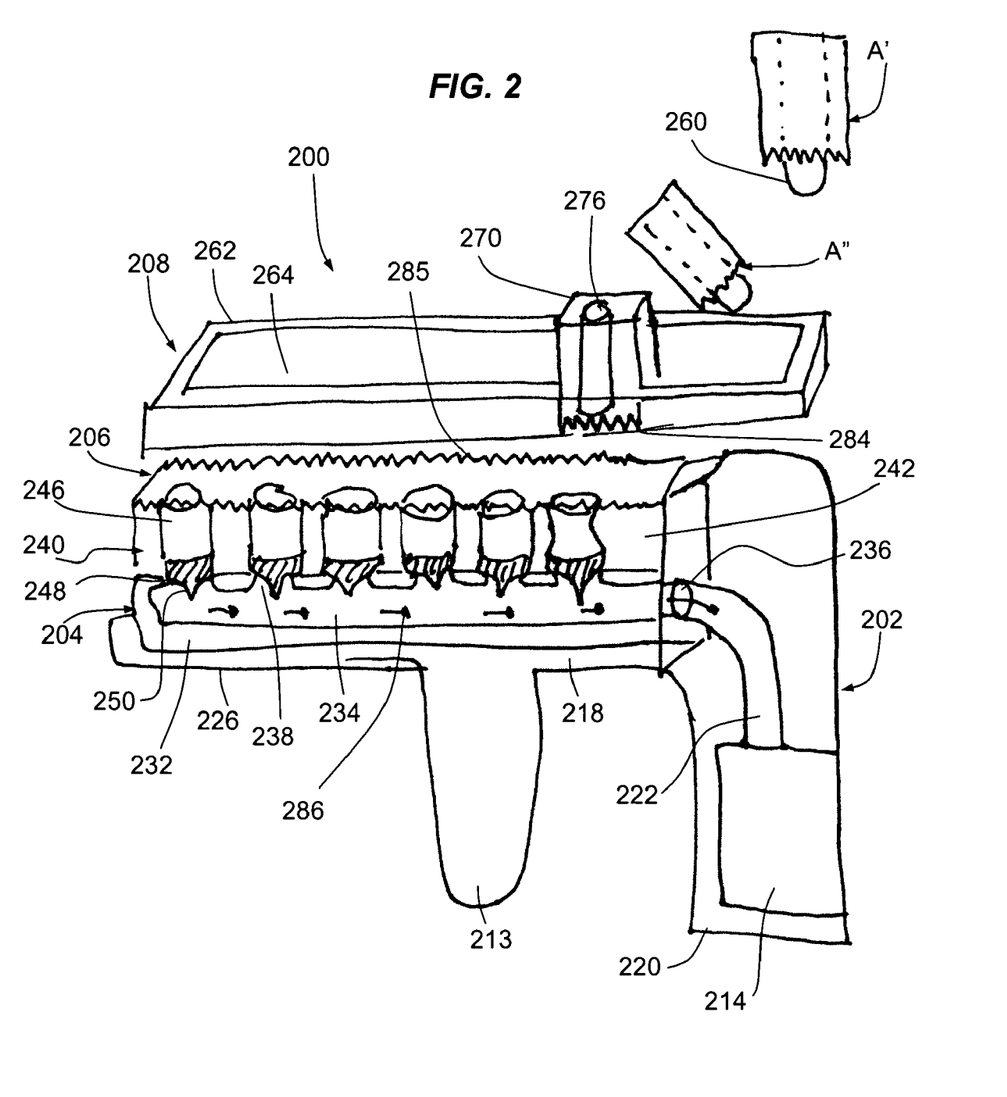
FIG. 2 is a perspective view of a biological sample collector having a slide case in accordance with an embodiment of the present invention.
Figure 3:
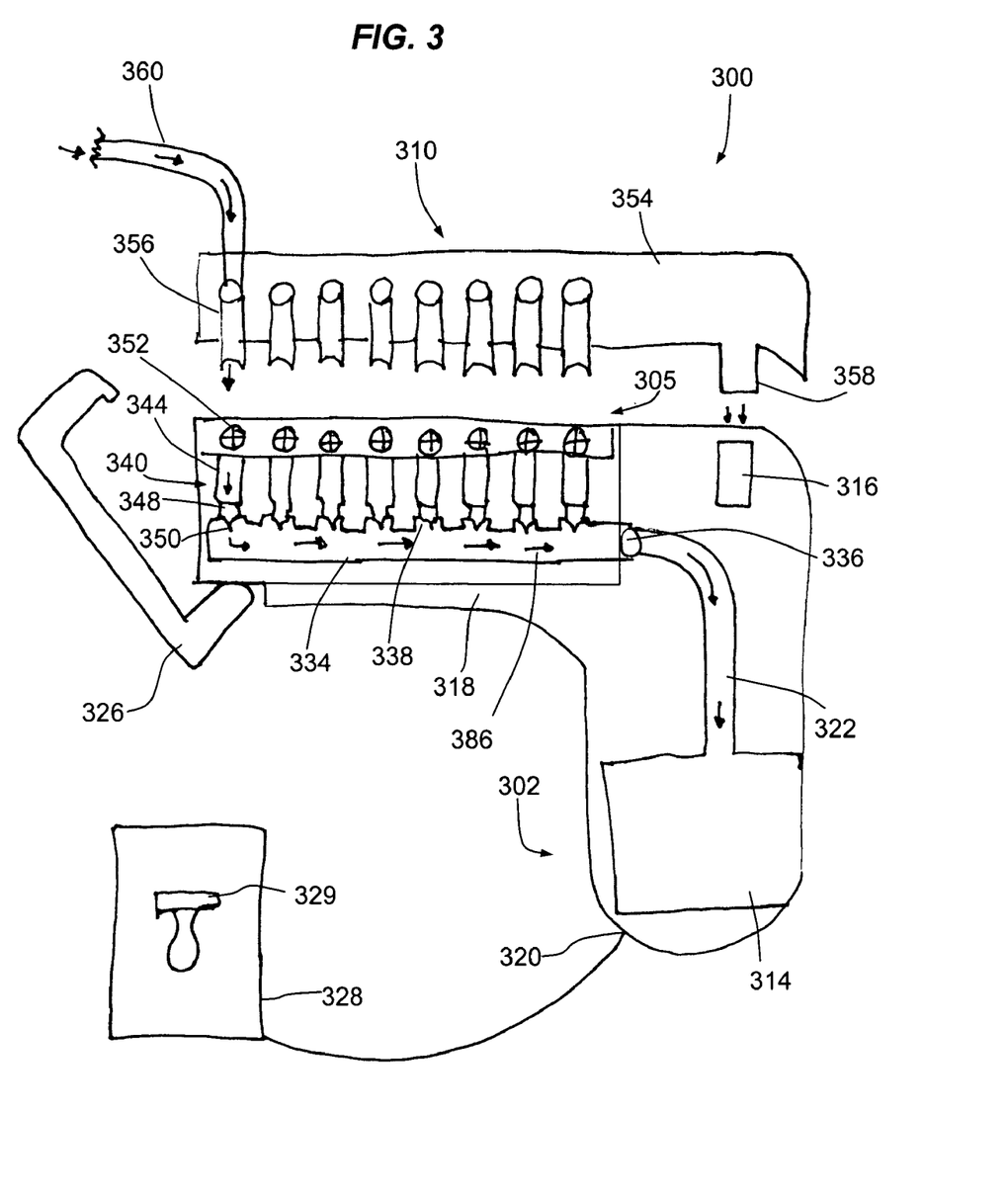
FIG. 3 is a perspective view of a biological sample collector having a tube case in accordance with an embodiment of the present invention.
Figure 4:
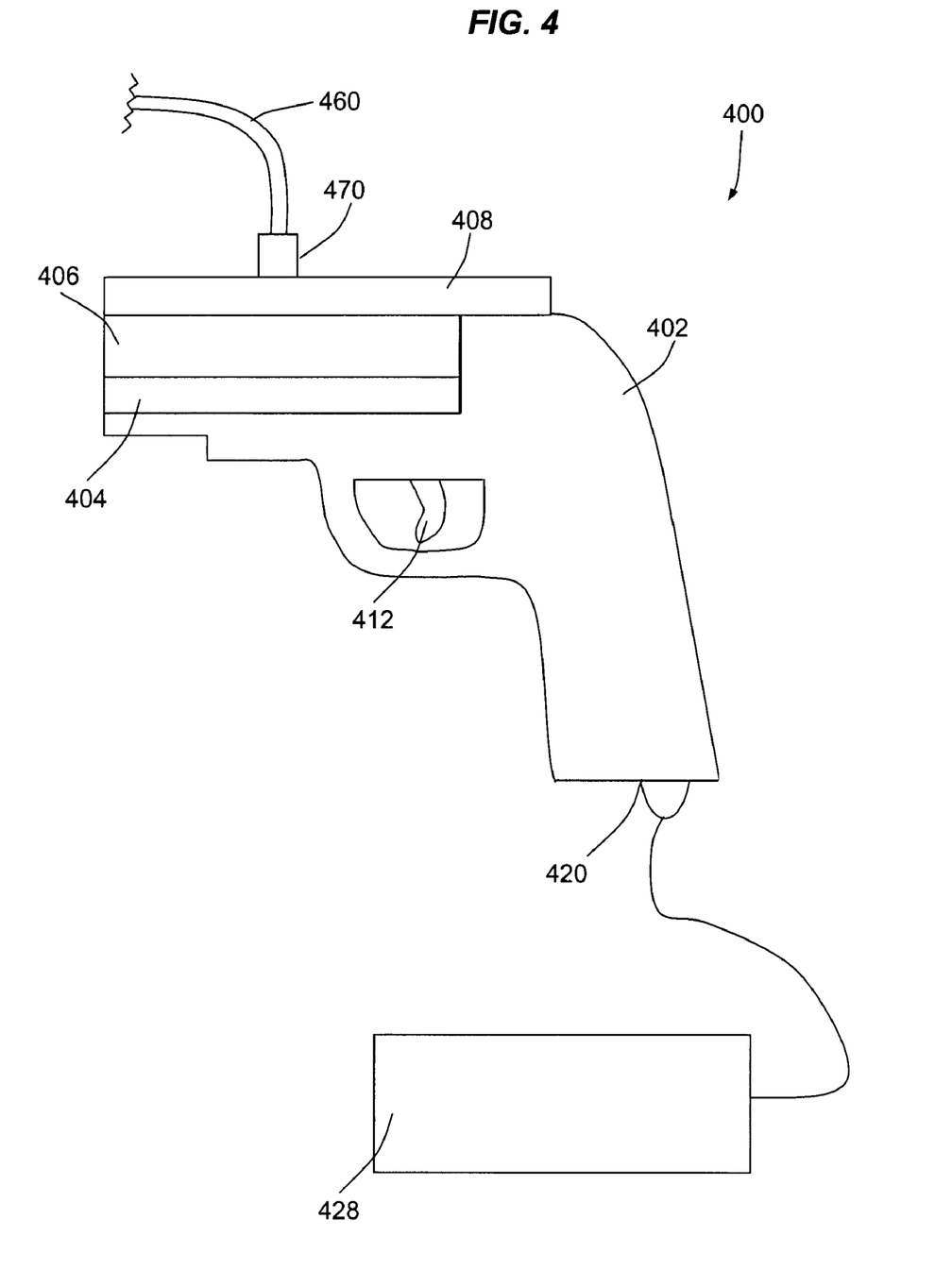
FIG. 4 is a side view of an assembled biological collector having a gun-shaped housing in accordance with an embodiment of the present invention.

Referring now to the embodiment depicted in FIG. 1, the biological sample collector 100 comprises a housing 102, manifold plate 104, filter plate 106 and slide case 108. Housing 102 comprises an actuator 112, air pump 114, notch 116, base extension 118, and a power port 120. Air pump 114 has a conduit 122 that opens out of housing 102 and air pump 114 is adjacent to vent grate 124. On base extension 118 there is a clamp 126. Connected to housing 102 through power port 120 is a power source 128 having an activation switch 130. Manifold plate 104 comprises a casing 132 that surrounds a pipe 134 having an outlet valve 136 and a plurality of intake valves 138. Filter plate 106 comprises a plurality of filter wells 140 in a strip 142. Each filter well 140 comprises a trap 144, shaft 146, filter 148 and tapered end 150. Positioned above trap 144 is a film barrier 152, described in further detail below with reference to FIG. 7. A tube 160 is inserted through the slide case 108. Slide case 108 comprises a lid 162 having grooves 168 for guiding hollow slider 170, described in further detail below with reference to FIGS. 5A-5E. Hollow slider 170 has an empty bore cylinder 176 through which tube 160 travels. Lid 162 also has a tenon 186 that engages notch 116 when biological sample collector 102 is assembled.

The embodiment depicted in FIG. 2 show a biological sample collector 200 comprising a housing 202 having a manifold plate 204 and filter plate 206 mounted thereon, as well slide case 208. Housing 202 comprises an actuator (not shown) on handle 213, air pump 214, base extension 218, and a power port 220. Air pump 214 has a conduit 222 that opens out of housing 202. On base extension 218 there is a clamp 226. Connected to housing 202 through power port 220 is a power source (not shown). Manifold plate 204 comprises a casing 232 that surrounds a pipe 234 having an outlet valve 236 and a plurality of intake valves 238. Filter plate 206 comprises a plurality of filter wells 240 in a strip 242. Each filter well 240 comprises a shaft 246, filter 248 and tapered end 250. A tube 260 is inserted through slide case 208. Slide case 208 comprises a lid 262 having an enclosed space 264 in which hollow slider 270 fits. Hollow slider 270 has an empty bore cylinder 276 through which tube 260 travels. Hollow slider 270 is shown in position A' removed from slide case 208 and position A" at an incline for loading into, slide case 208. Hollow slider 270 has teeth 284 for engaging corresponding teeth 285 on filter plate 206. Once engaged the teeth 284 and 285 may align and position hollow slider 270 to allow tube 260 to be inserted into filter well 240. Air may flow from tube 260 to air pump 214 as shown by arrows 286.

The embodiment in FIG. 3 shows a biological sample collector 300 comprising a housing 302, combined filter plate 305 and tube case 310. Housing 302 comprises an actuator (not shown), air pump 314, notch 316, base extension 318, and a power port 320. Air pump 314 has a conduit 322 that opens out of housing 302. On base extension 318 there is a clamp 326. Connected to housing 302 through power port 320 is a power source 328 having a clip 329. Combined filter plate 305 comprises a manifold pipe 334 having an outlet valve 336 and a plurality of intake valves 338 and a plurality of filter wells 340 aligned with intake valves 338. Each filter well 340 comprises a shaft 346, filter 348 and tapered end 350. Positioned above filter well 340 is a film barrier 352, described in further detail below with reference to FIG. 7. Tube case 310 comprises a lid 354 and tube holders 356 that extend through lid 354. Lid 354 has a tenon 358 that is inserted into notch 316 when biological sample collector 302 is assembled. This closed mortise-tenon joint aligns and secures lid 354 to housing 302. The number of tube holders 356 corresponds to the number of filter wells 340 in filter plate 306. Tube 360 is removably inserted in one of the tube holders 356. Air may flow from tube 360 to air pump 314 as shown by arrows 386.

In the embodiments of the present invention, a manifold plate is mounted to housing, filter plate is mounted to manifold plate, and slide case or tube case is mounted on filter plate and housing. These plate and case components are modular and may be interchanged or removed. For example filter plate may be removed once all the biological agents are deposited and a new filter plate may be inserted. Several different types of filter plates may be used, including 6, 8, 12, 48 or 96 filter-well plates. It should be understood that various combinations of the 8 and 12 filters well strips may be assembled into a 48 or 96 filter-well plate for use with robotic testing systems and devices. Depending on the filter plate, the size and configuration of the manifold plate may vary. In some embodiments of the present invention, such as the one shown in FIG. 3, the manifold plate and filter plate may be combined into one piece.

The biological sample collector may have several interchangeable components that may be readily assembled in field to collect the biological samples. In one embodiment biological sample collector may comprise a kit of multiple manifold plates, filter plates, slide cases and tube cases, as well as different types of housing shapes. Also, slide case may be interchanged with tube case depending on the application. This interchangeability provides a portable solution to biological sample collection that can adapt to a variety of collection situations, thus increasing the flexibility of use.

Another advantage of a modular design is that each of the plate and case components may be cleaned to reduce cross-contamination between collections of biological samples. Further modular components allow each plate and case component to be made of a disposable material, thus eliminating cross-contamination between collections of biological samples.

The housing may also have controls or a microprocessor (not shown) that operate components of housing. Actuator may be a button, switch, trigger, etc. that controls air pump. Air pump, which acts as a vacuum, sucks air in through conduit. Vent grate provides ventilation for air pump. The air pump may have a motor that operates at approximately 5-30 ft/min.

Base extension has one or more clamps for securing manifold plate, filter plate and slide case or tube case mounted thereon. Clamps may be any suitable releasable retention device that keeps the components mounted on base extension when in operation. Examples of suitable retention device include clamps, straps, fasteners, screws, grips, etc. In some embodiments there may separate clamps for each component mounted upon the base extension.

Connected to housing through power port may be a power source. Power source may include a battery or wall outlet. For portable applications, a battery may be used. Battery may have an activation switch and/or a clip. Conventional primary and secondary batteries may be used with embodiments of the present invention.

In one embodiment, housing is made of a translucent material, such as an acrylic material or other similar plastic material. A translucent material allows the operator of the biological sample collector to visually confirm that all the components are properly mounted. In addition, this allows for inspection of the biological sample deposited during use.

The shape and style of biological sample collector may vary. One example of a planar shape is shown in FIG. 1. Examples of a gun-shaped housing are shown in FIGS. 2-4. The embodiment in FIG. 4 shows a biological sample collector 400 comprising a gun-shaped housing 402, manifold plate 404, filter plate 406, slide case 408, actuator 412, power connector 420, power source 428, tube 460 and hollow slider 470. It should be understood that other housing shapes and styles may be used with embodiments of the present invention.

A manifold plate is one of the components mounted on the housing. The configuration of manifold plate may vary depending on the application. For example, there may be a network of pipes that connect the plurality of intake valves and the outlet valve. It should be understood that the number of intake valves may correspond to the design of filter plate. Each intake valve may have an annular sealing ring, such as an O-ring. This annular ring engages the filter well of the filter plate. When manifold plate is mounted to housing the outlet valve aligns with and sealingly engages the exposed orifice of the conduit connected to the air pump.

Any suitable filter plate may be used with embodiments of the present invention. The filter plate has a tapered end which sealingly engages with one of the intake valves when mounted to manifold plate. Filter may be made of a PDVF, Telphon™, or similar material. In one embodiment the filter may have a 0.45 μM or 0.8 μM pore size. The pore size should be sufficient to prevent any of the biological sample from entering the manifold pipe or air pump.

Tube is flexible and has an opened end that is used to collected biological samples from a treated environment. The open end may be a nozzle or similar vacuum port.

The closed mortise-tenon joint between notch and tenon aligns and secures the lid to the housing. This may act to further hold the manifold and filter plates to the housing. In some embodiments the hollow slider is driven by a mechanical motor. Mechanical motor may be within slide case and receives power from the power source through housing. The notch and tenon may also have an electrical mating connection that provides power and control through the housing. Thus, once the actuator on the housing is pressed the air pump may turn on and a control signal may be sent to the hollow slider to move to the next filter well.

Figure 5A:
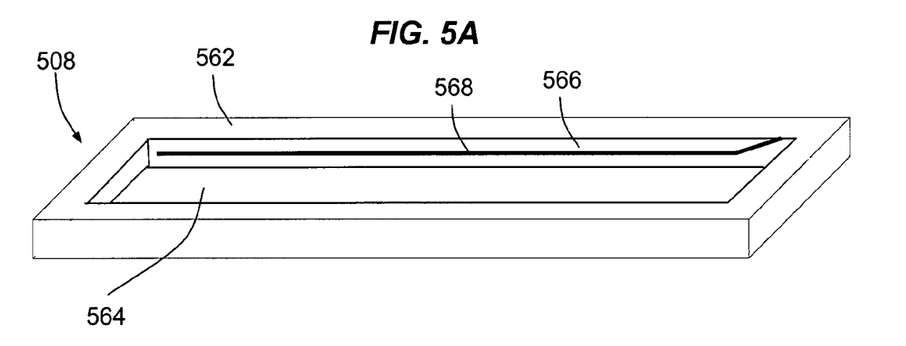
FIG. 5A is a perspective view of a slide case in accordance with an embodiment of the present invention.
Figure 5B:
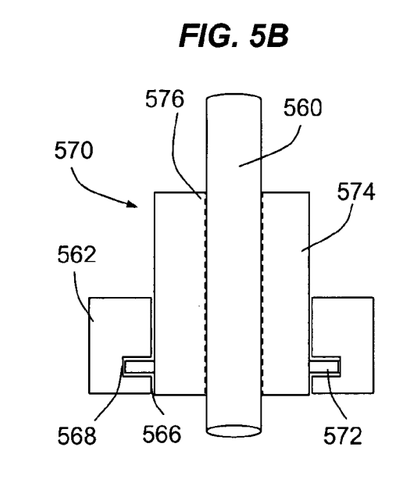
FIG. 5B is a cross-section view of a hollow slider within a slide case in accordance with an embodiment of the present invention.
Figure 5C:
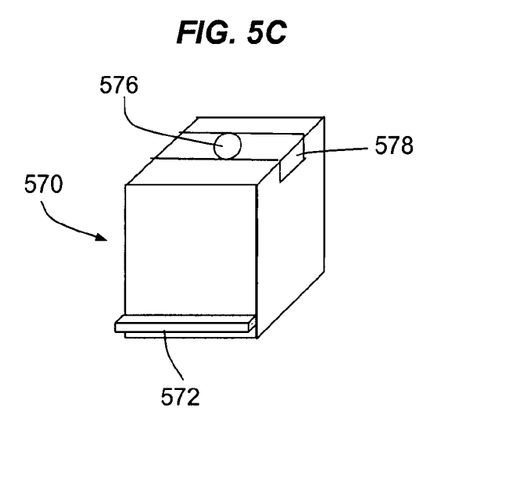
FIG. 5C is a perspective view of a hollow slider in accordance with an embodiment of the present invention.

FIG. 5A is a perspective view of a slide case 508 comprising a frame lid 562 with an enclosed space 564, inner walls 566, and grooves 568. Grooves 568 are cut into opposing inner walls 566. Grooves 568 may be inclined at one end of inner wall 566 to allow hollow slider 570 to be inserted into slide case 508.

Figure 5D:
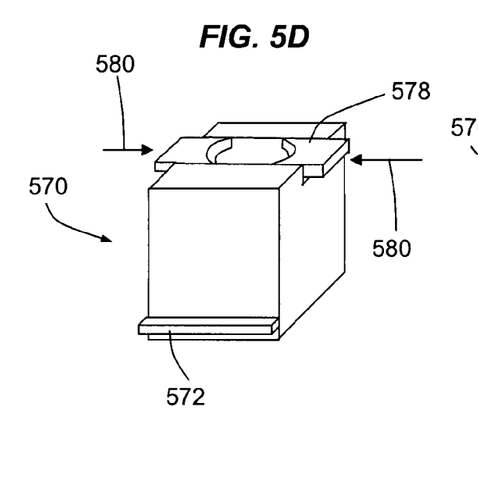
FIG. 5D is a perspective view of a hollow slider with the clamps retracted in accordance with an embodiment of the present invention.
Figure 5E:
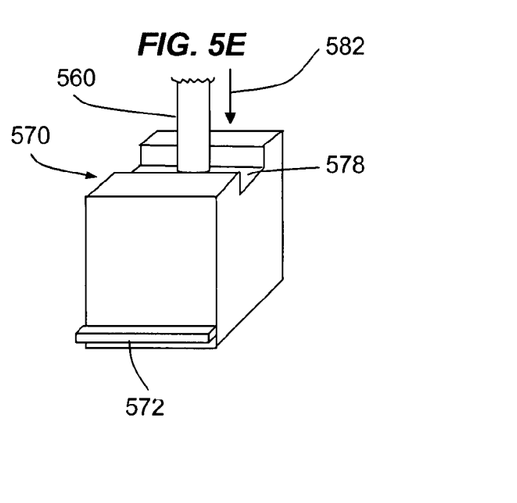
FIG. 5E is a perspective view of a hollow slider with the clamps pushed down in accordance with an embodiment of the present invention.

Within enclosed space 564, a hollow slider 570, shown in FIGS. 5B-5E, travels. Hollow slider 570 has guide rails 572 extending from body 574 through which a cylinder 576 having an empty bore extends. Guide rails 572 fit within grooves 568 and define a travel path of hollow slider 570. In one embodiment, when tube 560 is inserted into cylinder 576 pinchers 578 may be used to hold tube 560 in place. FIG. 5D shows pinchers 578 slid open when inserting tube 560 and closing shut as shown by arrows 580 to grasp tube 560. When open the bore size of cylinder 576 may increase. FIG. 5E shows that when tube 560 is pushed down, pinchers 578 may snap down as shown by arrow 582.

Hollow slider may be moved manually or by a mechanical means such as an electrical motor that drives a gears or wheels. Other mechanisms for moving the hollow slider are contemplated by this invention. In addition, there may be an alignment indicator next to each filter well to confirm the position of the hollow slider.

There may be a releasable mechanism for locking the hollow slider in place once aligned, such as the reciprocal teeth shown in FIG. 2. Other similar releasable locks may also be used with different embodiments of the present invention.

Figure 6:
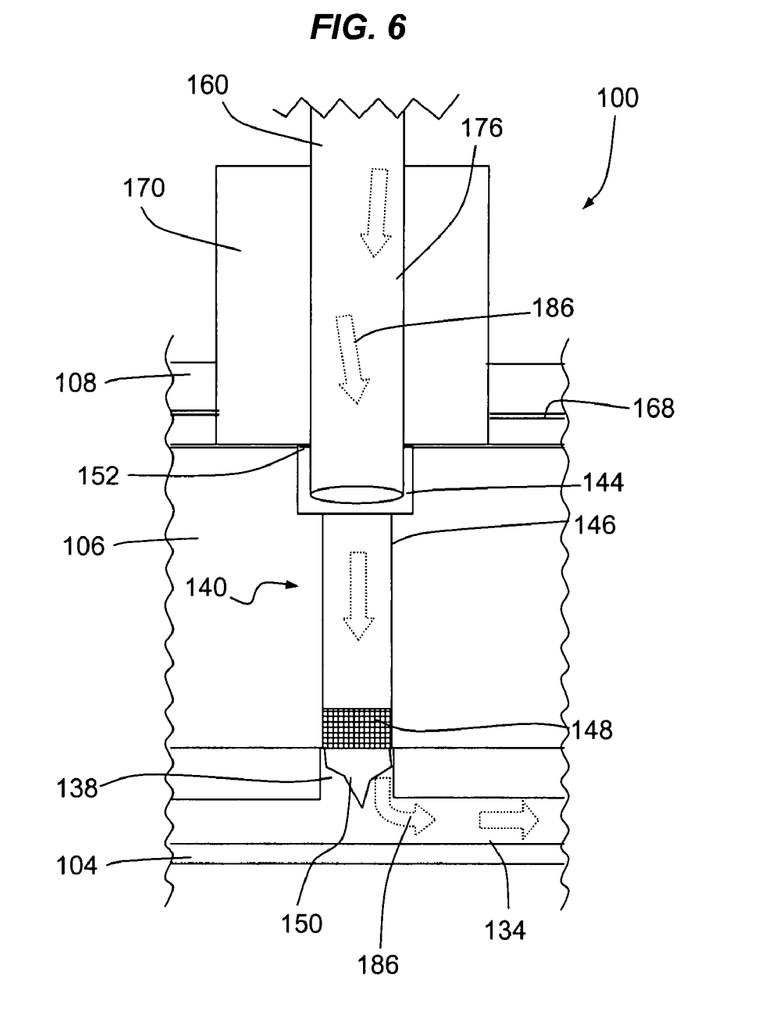
FIG. 6 is a detailed cross-section view of a tube aligned with a filter well in accordance with the embodiment shown in FIG. 1.

Returning to the embodiment shown in FIG. 1, a detailed cross-section view of a tube 160 inserted into trap 144 of a filter well 140 is shown in FIG. 6. Biological sample collector 100 has a slide case 108 mounted on filter plate 106 which is mounted on manifold plate 104. Tube 160 sealingly engages with film barrier 152 when inserted downward into trap 144. Arrows 186 indicate the direction of the air flow through tube 160, into filter well 140 and out through pipe 134. Biological samples (not shown) are deposited on filter 148. In one embodiment, when tube 160 is pushed down tube 160 slides within cylinder 176 of hollow slider 170. To create a proper seal, intake valve 138 sealingly engages with tapered end 150 of filter well 140. The seal between tube 160 and trap 144 is releasable once the biological sample is deposited on filter 148.

Figure 7:
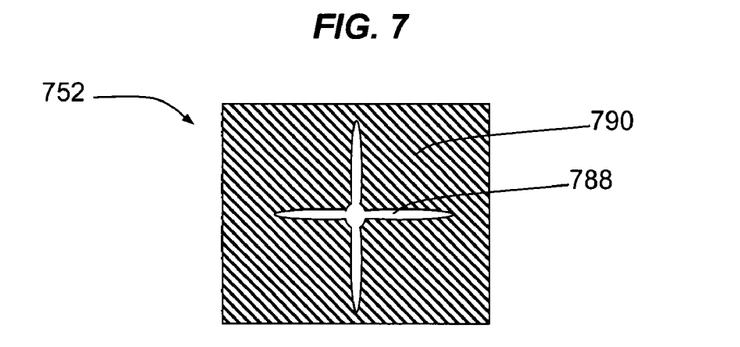
FIG. 7 is a top view of a film barrier in accordance with an embodiment of the present invention.

A top view of film barrier 752 is shown in FIG. 7. Film barrier 752 has several slots 788 for flexible flaps 790. Although four slots 788 are shown in FIG. 7, other embodiments may have a different number of slots from approximately 2-20 slots. Film barrier 752 is placed over the trap of each filter well to prevent aerosolization of any biological sample that is deposited into the filter well. In one embodiment, a plurality of film barriers 752 may be placed on a sheet (not shown) which correspondingly aligns with each of the filter wells. Film barrier 752 may be made of any suitable plastic material.

Figure 8A:
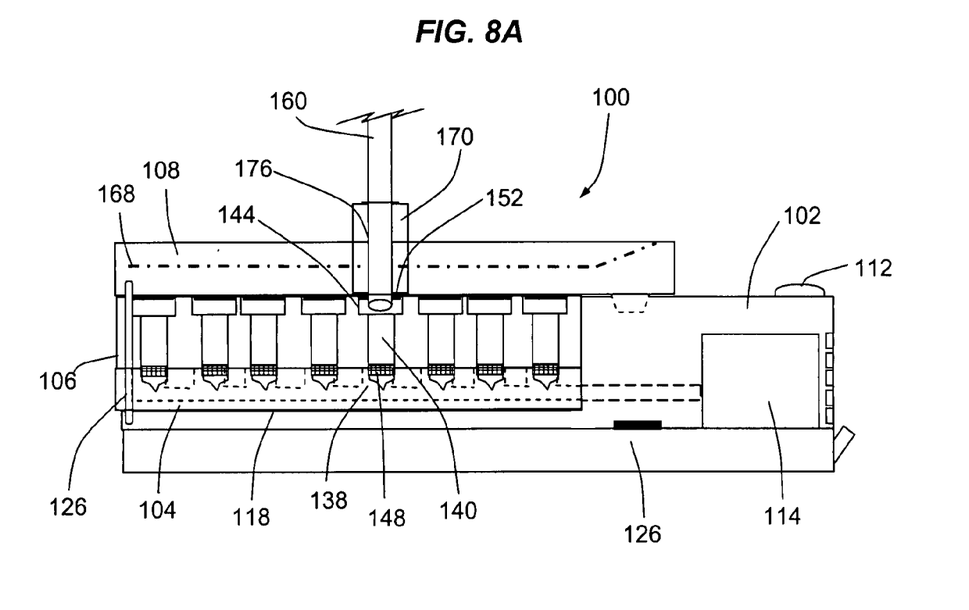
FIG. 8A is a side view of an assembled biological collector having a tube aligned with one filter well in accordance the embodiment shown in FIG. 1.
Figure 8B:
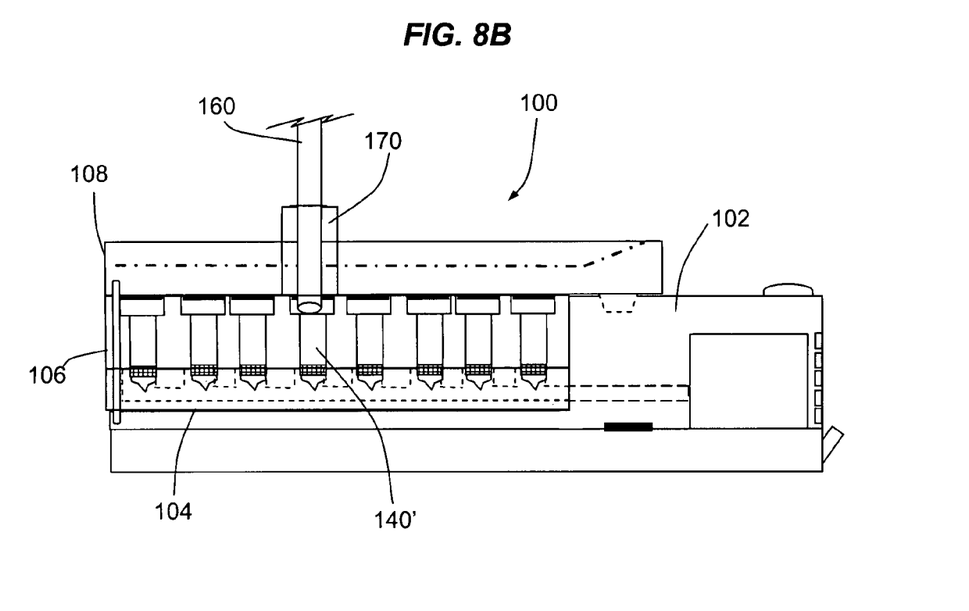
FIG. 8B is a side view of an assembled biological collector of FIG. 8A where the tube is aligned with a second filter well in accordance with the embodiment shown in FIG. 1.

FIGS. 8A and 8B illustrate two loading positions of hollow slider 170 of the embodiment shown in FIG. 1 in accordance with an exemplary method of the present invention. Prior to collecting the biological samples, biological sample collector 100 is assembled. Manifold plate 104 is mounted on a base extension 118, and filter plate 106 is mounted on top of manifold plate 104. It should be understood that the selection of manifold plate 104 and filter plate 106 is such that the number of filter wells 140 corresponds to the intake valves 138. Next, slide case 108 is placed over filter plate 106 and housing 102. Clamp 126 secures each of these plates when mounted to housing 102.

Next, tube 160 is loaded into cylinder 176 of hollow slider 170. Hollow slider 170 travels along grooves 168 in slide case 108. Once aligned with a filter well 140, tube 160 is pushed down through film barrier 152 into trap 144 and air pump 114 is activated by actuator 112. Power from power source 126 drives the motor of air pump 114. Air pump 114 sucks the biological sample through tube 160 and deposits the biological samples collected on to filter 148. Once the biological sample is deposited, the vacuum shuts off and tube 160 is retracted out of the trap 160 through the film barrier 152. Hollow slider 170 travels along grooves to the next filter well 140' shown in FIG. 8B and the process is repeated. This continues until each filter well is loaded with biological samples. Next clamps 126 are released and slide case 108 is removed so that the filter plate 106 may be replaced with an empty filter plate 106. Each of the loaded filter plates may be assembled into a larger plate for testing of the collected biological sample.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A biological sample collector comprising:
   a manifold plate for mounting a filter plate thereon, the filter plate having a plurality of filter wells therein;
   a hollow slider for engaging and positioning a tube that slides therethrough; and
   a slide case within which the hollow slider travels to allow the tube to be aligned with a selected filter well of the plurality of filter wells, wherein when the tube is aligned with the selected filter well, the tube is pushed through the hollow slider and into the selected filter well to sealingly engage the selected filter well and to allow the tube to deposit a biological sample onto a filter in the bottom of the selected filter well.

2. The biological sample collector of claim 1, further comprising a suction means for pulling the deposited biological sample from the tube and onto the filter.

3. The biological sample collector of claim 2, wherein the manifold plate comprises a network of pipes for fluidly connecting the suction means to the tube.

4. The biological sample collector of claim 1, further comprising a film barrier that is disposed between the selected filter well and hollow slider.

5. The biological sample collector of claim 1, wherein the hollow slider has a releasable locking means for securing to the selected filter well.

6. The biological sample collector of claim 1, further comprising a housing on which the manifold plate, filter plate and slide case are mounted.

7. The biological sample collector of claim 6, wherein the manifold plate is interchangeably mounted to the housing.

8. The biological sample collector of claim 6, wherein the filter plate is interchangeably mounted to the housing.

9. The biological sample collector of claim 6, wherein the slide case is interchangeably mounted to the housing.

10. A biological sample collector comprising:
    a suction means in fluid communication with a filter plate, wherein the filter plate comprises a plurality of filter wells;
    a hollow slider for engaging and positioning a tube that slides therethrough; and
    a slide case within which the hollow slider travels to allow the tube to be aligned with a selected filter well of the plurality of filter wells, wherein when the tube is aligned with the selected filter well, the tube is pushed through the hollow slider and into the selected filter well to sealingly engage the selected filter well and to allow the suction means to pull a biological sample from the tube that is deposited on a filter in the bottom of the selected filter well.

11. The biological sample collector of claim 10, further comprising a manifold plate upon which the filter plate is mounted.

12. The biological sample collector of claim 11, wherein the manifold plate is sealingly engaged with an exposed conduit of the suction means.

13. The biological sample collector of claim 11, wherein the manifold plate comprises a network of pipes for fluidly connecting the suction means to the tube.

14. The biological sample collector of claim 10, further comprising a film barrier that is disposed between the selected filter well and hollow slider.

15. The biological sample collector of claim 10, wherein the hollow slider has a releasable locking means for securing to the selected filter well.

16. The biological sample collector of claim 10, further comprising a housing in which the suction means is housed.

17. The biological sample collector of claim 16, wherein the filter plate is interchangeably mounted to the housing.

18. The biological sample collector of claim 16, wherein the slide case is interchangeably mounted to the housing.

19. A biological sample collector comprising:
    a suction means within a housing;
    a manifold plate mounted on the housing for mounting a filter plate thereon, the filter plate having a plurality of filter wells therein; and
    a tube case having a plurality of tube holders each for engaging and positioning a tube that slides through a selected tube holder, wherein when the tube is aligned with a selected filter well of the plurality of filter wells, the tube is pushed through the selected tube holder and into the selected filter well to sealingly engage the selected filter well and to allow the suction means to pull from the tube a biological sample that is deposited on a filter in the bottom of the selected filter well.

20. The biological sample collector of claim 19, wherein the suction means is in fluid communication with the tube.

21. The biological sample collector of claim 19, wherein the manifold plate comprises a network of pipes.

22. The biological sample collector of claim 19, further comprising a film barrier that is disposed between the selected filter well and hollow slider.

23. The biological sample collector of claim 19, wherein the manifold plate is interchangeably mounted to the housing.

24. The biological sample collector of claim 19, wherein the filter plate is interchangeably mounted to the housing.

25. The biological sample collector of claim 19, wherein the tube case is interchangeably mounted to the housing.

* * * * *